US010520456B2

(12) United States Patent
Tezuka et al.

(10) Patent No.: US 10,520,456 B2
(45) Date of Patent: Dec. 31, 2019

(54) COMBUSTION EXPERIMENT DEVICE

(71) Applicants: Tohoku University, Sendai-shi, Miyagi (JP); IHI Corporation, Tokyo (JP)

(72) Inventors: Takuya Tezuka, Sendai (JP); Hisashi Nakamura, Sendai (JP); Kaoru Maruta, Sendai (JP); Soichiro Kato, Tokyo (JP); Shintaro Ito, Tokyo (JP)

(73) Assignees: TOHOKU UNIVERSITY, Sendai-Shi, Miyagi (JP); IHI CORPORATION, Tokyo (JP)

( * ) Notice: Subject to any disclaimer, the term of this patent is extended or adjusted under 35 U.S.C. 154(b) by 530 days.

(21) Appl. No.: 15/346,962

(22) Filed: Nov. 9, 2016

(65) Prior Publication Data
US 2017/0052134 A1 Feb. 23, 2017

Related U.S. Application Data

(63) Continuation of application No. PCT/JP2015/063785, filed on May 13, 2015.

(30) Foreign Application Priority Data

May 13, 2014 (JP) .................................. 2014-099863

(51) Int. Cl.
*G01N 25/52* (2006.01)
*G01N 25/50* (2006.01)

(52) U.S. Cl.
CPC ............. *G01N 25/52* (2013.01); *G01N 25/50* (2013.01)

(58) Field of Classification Search
CPC ............................... G01N 25/52; G01N 25/50
See application file for complete search history.

(56) References Cited

U.S. PATENT DOCUMENTS 3,987,661 A * 10/1976 Kamp .................... G01N 25/50
   374/8
5,246,667 A * 9/1993 Hemzy ................... F27D 7/06
   422/78

(Continued)

FOREIGN PATENT DOCUMENTS

EP      2 642 280 A1    9/2013
JP     2010-112892 A    5/2010

(Continued)

OTHER PUBLICATIONS

Akira Yamamoto et al, "Stabilized three-stage oxidation of gaseous n-heptane/air mixture in a micro flow reactor with a controlled temperature profile," Proceedings of the Combustion Institute, vol. 33, No. 2, Aug. 7, 2010 (Aug. 7, 2010), pp. 3259-3266, XP028164943, ISSN: 1540-7489, DOI: 10.1016/J.PROCI.2010.05.004 (8 pages).

(Continued)

*Primary Examiner* — Freddie Kirkland, III
(74) *Attorney, Agent, or Firm* — Rothwell, Figg, Ernst & Manbeck, P.C.

(57) ABSTRACT

Provided is a combustion experiment device, which includes a reaction tube into which a sample fluid flows and to which a temperature gradient in which a temperature rises toward a downstream side is imparted, and a burner part that is configured to flow a combustible gas along and around the reaction tube from the downstream side to an upstream side of the reaction tube and to maintain a flame surrounding the reaction tube from the outside in a radial direction of the reaction tube.

11 Claims, 9 Drawing Sheets

(56) References Cited

U.S. PATENT DOCUMENTS

| | | | | |
|---|---|---|---|---|
| 7,174,797 | B2 * | 2/2007 | Brostmeyer | G01M 15/14 |
| | | | | 73/865.6 |
| 8,281,649 | B1 * | 10/2012 | Crutchfield | G01M 99/002 |
| | | | | 73/112.01 |
| 9,562,868 | B2 * | 2/2017 | Maruta | G01N 25/52 |
| 2004/0216535 | A1 | 11/2004 | Brostmeyer et al. | |
| 2013/0235898 | A1 | 9/2013 | Maruta et al. | |

FOREIGN PATENT DOCUMENTS

| | | |
|---|---|---|
| JP | 2011-58746 A | 3/2011 |
| JP | 2012-108036 A | 6/2012 |
| JP | 5453221 B2 | 3/2014 |
| KR | 10-2011-0054277 A | 5/2011 |

OTHER PUBLICATIONS

Graeme M.G. Watson et al, "The effect of chemical energy release on heat transfer from flames in small channels," Combustion and Flame, vol. 159, No. 3, Nov. 19, 2011 (Nov. 19, 2011), pp. 1239-1252, XP055408227, Amsterdam, NL ISSN: 0010-2180, DOI: 10.1016/j.combustflame.2011.10.021 (14 pages).

* cited by examiner

COMBUSTION EXPERIMENT DEVICE

Embodiments described herein relates to a combustion experiment device.

This application is a continuation application based on a PCT Patent Application No. PCT/JP2015/063785, filed on May 13, 2015, whose priority is claimed on Japanese Patent Application No. 2014-99863, filed on May 13, 2014. The contents of both the PCT Application and the Japanese Application are incorporated herein by reference.

TECHNICAL FIELD

Background Art

In recent years, as shown in, for example, Patent Document 1, a combustion experiment device is proposed in which a flammable sample fluid flows into a reaction tube to which a temperature gradient in which a temperature increases downstream is imparted, and an ignition temperature, or the like are measured on the basis of a position at which a flame is formed. For example, in Patent Document 1, a heater is installed around the reaction tube, and the temperature gradient is imparted to the reaction tube by heating with this heater.

CITATION LIST

Patent Document

[Patent Document 1]
Japanese Unexamined Patent Application, First Publication No. 2012-108036

SUMMARY

Meanwhile, a temperature that can be given to a reaction tube in the case of heating caused by a heater has an upper limit of about 1000° C. For this reason, when an experiment is performed on combustion characteristics at a higher temperature range, it is considered that the reaction tube is heated by heating the reaction tube from the outside by a flame formed a burner or the like.

However, when the reaction tube is heated by the flame formed by the burner or the like, the reaction tube is generally heated from one direction. For example, the reaction tube is disposed such that an internal flow passage becomes horizontal, and this reaction tube is heated from below. For this reason, the burner side of the reaction tube has a higher temperature than the opposite side, and a deviation in temperature occurs in the reaction tube in a radial direction.

To accurately measure an ignition temperature, or the like of a sample fluid, it is necessary to know what kind of temperature gradient is imparted to the reaction tube in advance. However, as described above, if the deviation in temperature occurs in the radial direction of the reaction tube, a difference between data of a pre-stored temperature gradient and the actual temperature occurs. For this reason, a slight deviation occurs in a relation between a flame position in the reaction tube and an actual temperature of the reaction tube, and measurement accuracy is reduced.

The present disclosure was conceived in view of the aforementioned problems, and an object of the present disclosure is to prevent deviation in temperature from occurring in a reaction tube in a radial direction of the reaction tube to increase measurement accuracy in a combustion experiment device that imparts a temperature gradient to the reaction tube to measure combustion characteristics of a sample fluid.

As means for solving the above problems, the present disclosure adopts the following constitutions.

A first aspect according to the present disclosure is a combustion experiment device includes: a reaction tube into which a sample fluid flows and to which a temperature gradient in which a temperature rises toward a downstream side is imparted; and a burner part configured to flow a combustible gas along and around the reaction tube from the downstream side to an upstream side of the reaction tube and to maintain a flame surrounding the reaction tube from an outside of the reaction tube in a radial direction.

According to the present disclosure, the flame surrounding the reaction tube from the outside of the reaction tube in the radial direction is formed by the combustible gas that is flowed around the reaction tube from the downstream side toward the upstream side of the reaction tube by the burner part. For this reason, the reaction tube is heated from the outside in the radial direction over an entire area in a circumferential direction by the flame. Therefore, according to the present embodiment, it is possible to prevent a deviation in temperature from occurring within the reaction tube in the radial direction of the reaction tube. Consequently, according to the present embodiment, in the combustion experiment device that imparts the temperature gradient to the reaction tube to measure combustion characteristics of the sample fluid, it is possible to prevent the deviation in temperature from occurring within the reaction tube in the radial direction of the reaction tube and improve measurement accuracy. Further, according to the present embodiment, since the reaction tube is heated by a flame formed by the burner part, the temperature of the reaction tube can be raised to a high temperature range that cannot be realized by a heater. For this reason, a sample fluid that shows no reaction until the temperature reaches this high temperature range can be evaluated.

DESCRIPTION OF EMBODIMENTS

Figure 1A:
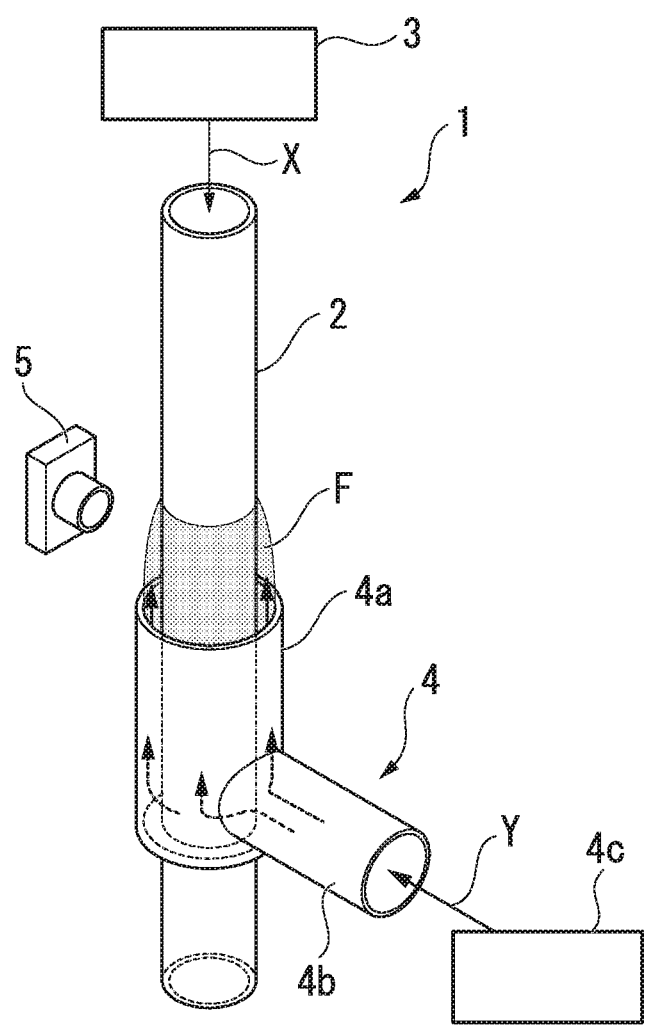
FIG. 1A is a perspective view schematically showing an overall constitution of a combustion experiment device in a first embodiment of the present disclosure.

Hereinafter, embodiments of a combustion experiment device according to the present disclosure will be described with reference to the drawings. In the drawings below, the scale of each member is adequately changed to have each member be a recognizable size.

First Embodiment

Figure 1B:
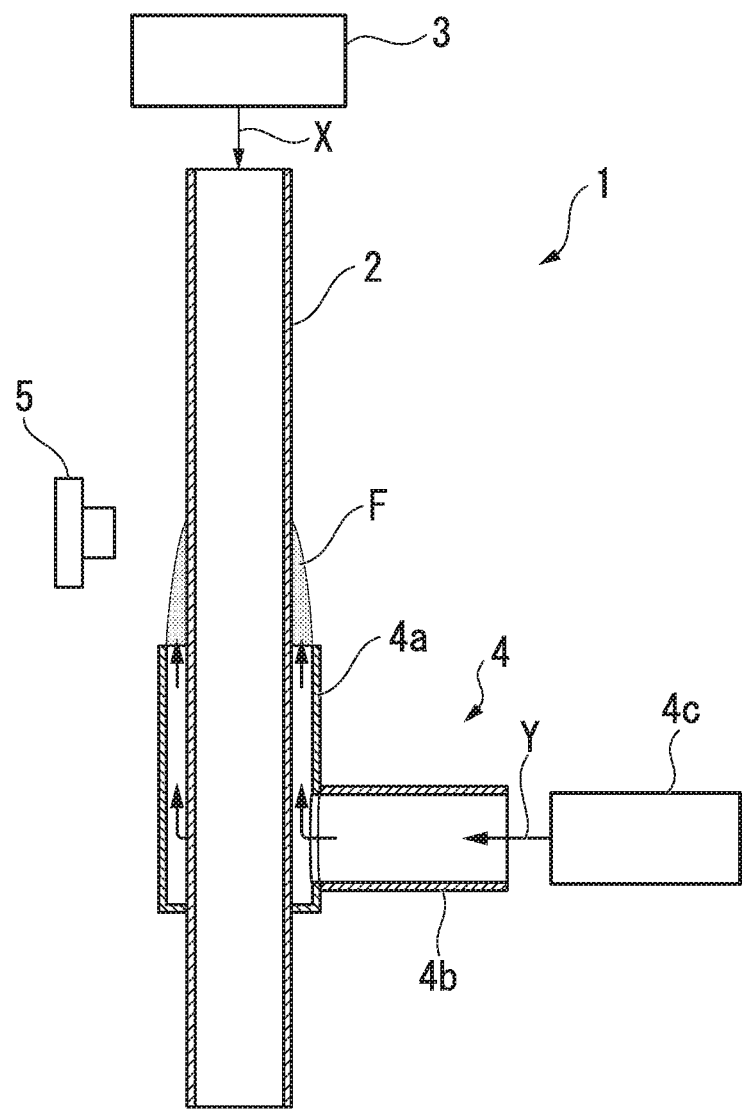
FIG. 1B is a longitudinal sectional view schematically showing the overall constitution of the combustion experiment device in the first embodiment of the present disclosure.

FIGS. 1A and 1B are schematic views showing a combustion experiment device 1 of the present embodiment wherein FIG. 1A is a perspective view and FIG. 1B is a longitudinal sectional view. As shown in these figures, the combustion experiment device 1 is provided with a reaction tube 2, a sample evaluation gas feeder 3, a burner part 4, and a camera 5.

The reaction tube 2 is a linear tube disposed by a support (not shown) such that an axial direction (a flow direction) thereof is parallel to a vertical direction. This reaction tube 2 is formed of a material (e.g. quartz glass) transparent to light emitted from a flame formed therein. In this reaction tube 2, a temperature gradient in which a temperature is raised toward a downstream side (a lower side in FIGS. 1A and 1B) by the burner part 4 is imparted, and a sample evaluation gas (a sample fluid) X is fed from an upstream side (an upper side in FIGS. 1A and 1B) by the sample evaluation gas feeder 3.

An internal flow passage of this reaction tube 2 is set to a diameter smaller than that of a quenching diameter at room temperature. To spread a flame within the flow passage, a cross-sectional area of the flow passage is required to extend to some degree. When the flow passage cross-sectional area is small, a flame is not spread. Here, the aforementioned quenching diameter refers to a diameter providing a cross-sectional area in which a formed flame cannot be spread.

The sample evaluation gas feeder 3 is connected to an upper end of the reaction tube 2 and feeds the sample evaluation gas X from the upper end toward a lower end of the reaction tube 2. This sample evaluation gas feeder 3 feeds a mixed gas in which a fuel and an oxidant are mixed and which acts as the sample evaluation gas X to the reaction tube 2.

The burner part 4 is provided with a nozzle part 4a, a feed tube 4b, and a hydrogen gas feeder 4c. The nozzle part 4a is a cylindrical part that covers the reaction tube 2 from the outside of the reaction tube 2 in a radial direction. The nozzle part 4a has an upper end acting as an opened end and a lower end acting as a closed end. The nozzle part 4a having this constitution ejects a combustible gas Y toward the upstream side (the upper side) of the reaction tube 2. That is, the burner part 4 flows the combustible gas Y along and around the reaction tube 2 from the downstream side toward the upstream side of the reaction tube 2.

Figure 2A:
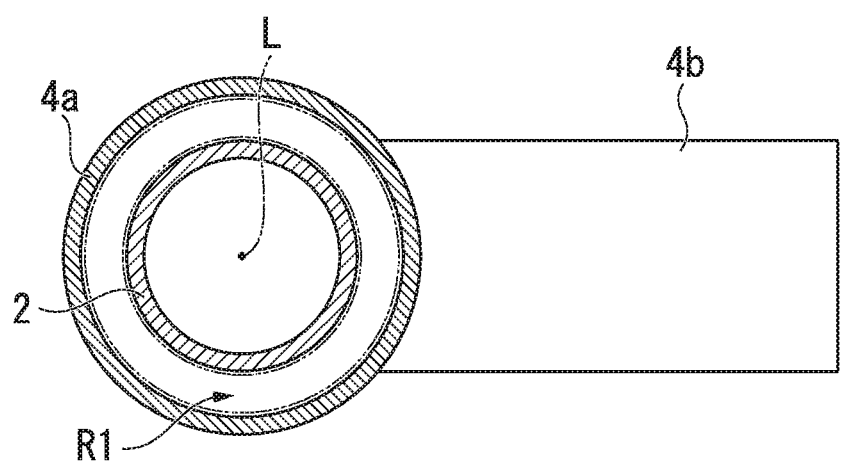
FIG. 2A is a cross-sectional view including a reaction tube and a nozzle part provided for the combustion experiment device in the first embodiment of the present disclosure.

FIG. 2A is a cross-sectional view of the nozzle part 4a and the reaction tube 2. As shown in this figure, the nozzle part 4a is a circular tube disposed to be coaxial with respect to an axis L of the reaction tube 2. Thus, an annular flow passage R1 having a uniform size in a circumferential direction is formed between the reaction tube 2 and the nozzle part 4a. For this reason, the combustible gas Y passing through this annular flow passage R1 to be injected from the upper end of the nozzle part 4a is uniformly injected around the reaction tube 2 when viewed in a direction running along the axis L of the reaction tube 2.

Figure 2B:
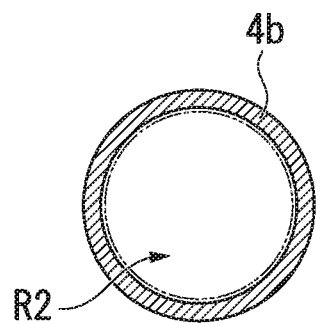
FIG. 2B is a cross-sectional view including a feed tube provided for the combustion experiment device in the first embodiment of the present disclosure.

The feed tube 4b is a tube that is connected to the nozzle part 4a from the outside of the nozzle part 4a in the radial direction and is intended to feed the combustible gas Y to the inside of the nozzle part 4a. FIG. 2B is a cross-sectional view of the feed tube 4b. As shown in this figure, the inside of the feed tube 4b is provided with a flow passage R2 guiding the combustible gas Y. A cross-sectional area of this flow passage R2 is set to be greater than that of the annular flow passage R1 shown in FIG. 2A. Thus, an inlet area of the nozzle part 4a for the combustible gas Y is greater than an outlet area, and the combustible gas Y is easily uniformly distributed in the nozzle part 4a. Therefore, the combustible gas Y can be more uniformly injected around the reaction tube 2.

The hydrogen gas feeder 4c feeds hydrogen gas acting as the combustible gas Y to the feed tube 4b. For this reason, in the present embodiment, the hydrogen gas that is a flammable gas is used as the combustible gas Y. That is, a combustion assisting gas such as oxygen is not contained in the combustible gas Y.

This burner part 4 feeds the hydrogen gas acting as the combustible gas Y from the hydrogen gas feeder 4c to the nozzle part 4a through the feed tube 4b, and flows the combustible gas Y from the nozzle part 4a around the reaction tube 2. In this way, the burner part 4 continues to flow the combustible gas Y, thereby maintaining a flame F to be described below.

The camera 5 is supported and disposed beside the reaction tube 2 by a support (not shown) and images a flame formed within the reaction tube 2 from the outside of the reaction tube 2, thereby obtaining information about a position of the flame in the reaction tube 2. Since a quantity of emitted light of the flame formed within the reaction tube 2 is small, the camera 5 preferably sets a long exposure time as needed to capture an image.

In this combustion experiment device 1 of the present embodiment, the combustible gas Y is fed from the hydrogen gas feeder 4c to the nozzle part 4a through the feed tube 4b, and this combustible gas Y is ejected from the upper end of the nozzle part 4a surrounding the reaction tube 2. That is, the combustible gas Y flows along and around the reaction tube 2 from the downstream side toward the upstream side of the reaction tube 2 by means of the burner part 4.

In this state, when the combustible gas Y ejected from the nozzle part 4a is ignited by an igniter (not shown), the flame F that, as shown in FIGS. 1A and 1B, surrounds the reaction tube 2 from the outside in the radial direction and is tapered toward the upper end of the reaction tube 2 is formed. This flame F is maintained as the combustible gas Y is continuously fed from the burner part 4. Here, in the present embodiment, the combustible gas Y ejected from the nozzle part 4a is used as the hydrogen gas that is a flammable gas free of a combustion assisting gas. For this reason, the flame F is a diffusion flame formed by diffusion combustion in which hydrogen gas is burnt by oxygen which is fed from the outside of the flame F.

When the flame F is formed in this way, a temperature gradient in which a temperature becomes high at a position at which the flame F is formed and becomes low toward the upstream side (the upper side) of the reaction tube 2 is imparted to the reaction tube 2. The sample evaluation gas X is fed from the upstream side to the reaction tube 2 to which this temperature gradient is imparted by the sample evaluation gas feeder 3. The sample evaluation gas X fed to the reaction tube 2 is raised in temperature as it approaches the downstream side of the reaction tube 2, and is ignited at a place exceeding a given temperature. Thus, the flame is formed inside the reaction tube 2. Then, the flame formed inside this reaction tube 2 is imaged by the camera 5, and an ignition temperature of the sample evaluation gas X is found from the position of the imaged flame and information about the temperature gradient imparted to the reaction tube 2.

According to the combustion experiment device 1 of the present embodiment as described above, the combustible gas Y flows around the reaction tube 2 from the downstream side toward the upstream side of the reaction tube 2 by means of the burner part 4. Thereby, the flame F surrounding the reaction tube 2 from the outside in the radial direction is formed. For this reason, the reaction tube 2 is heated from the outside in the radial direction over an entire area in a circumferential direction by the flame F. Therefore, according to the combustion experiment device 1 of the present embodiment, it is possible to prevent a deviation in temperature from occurring within the reaction tube 2 in the radial direction of the reaction tube 2. Consequently, according to the combustion experiment device 1 of the present embodiment, it is possible to prevent the deviation in temperature from occurring within the reaction tube 2 in the radial direction of the reaction tube 2 and to improve measurement accuracy.

In the combustion experiment device 1 of the present embodiment, the burner part 4 flows the hydrogen gas that acts as the combustible gas Y and is the flammable gas free of a combustion assisting gas. For this reason, the flame F becomes the diffusion flame. Thus, it is possible to prevent the flame from intruding into the nozzle part 4a. Therefore, the combustion experiment device 1 is, for example, disposed in a pressurized container, and an experiment may be performed under high pressure.

In the combustion experiment device 1 of the present embodiment, the burner part 4 is provided with the nozzle part 4a that covers the reaction tube 2 from the outside in the radial direction and ejects the combustible gas Y, and the feed tube 4b that is connected to the nozzle part 4a and feeds the combustible gas Y to the nozzle part 4a. For this reason, the combustible gas Y can be fed around the reaction tube 2 with a simple constitution.

Second Embodiment

Next, a second embodiment of the present embodiment will be described. In the description of the present embodiment, a description of the same parts as in the first embodiment will be omitted or simplified.

Figure 3A:
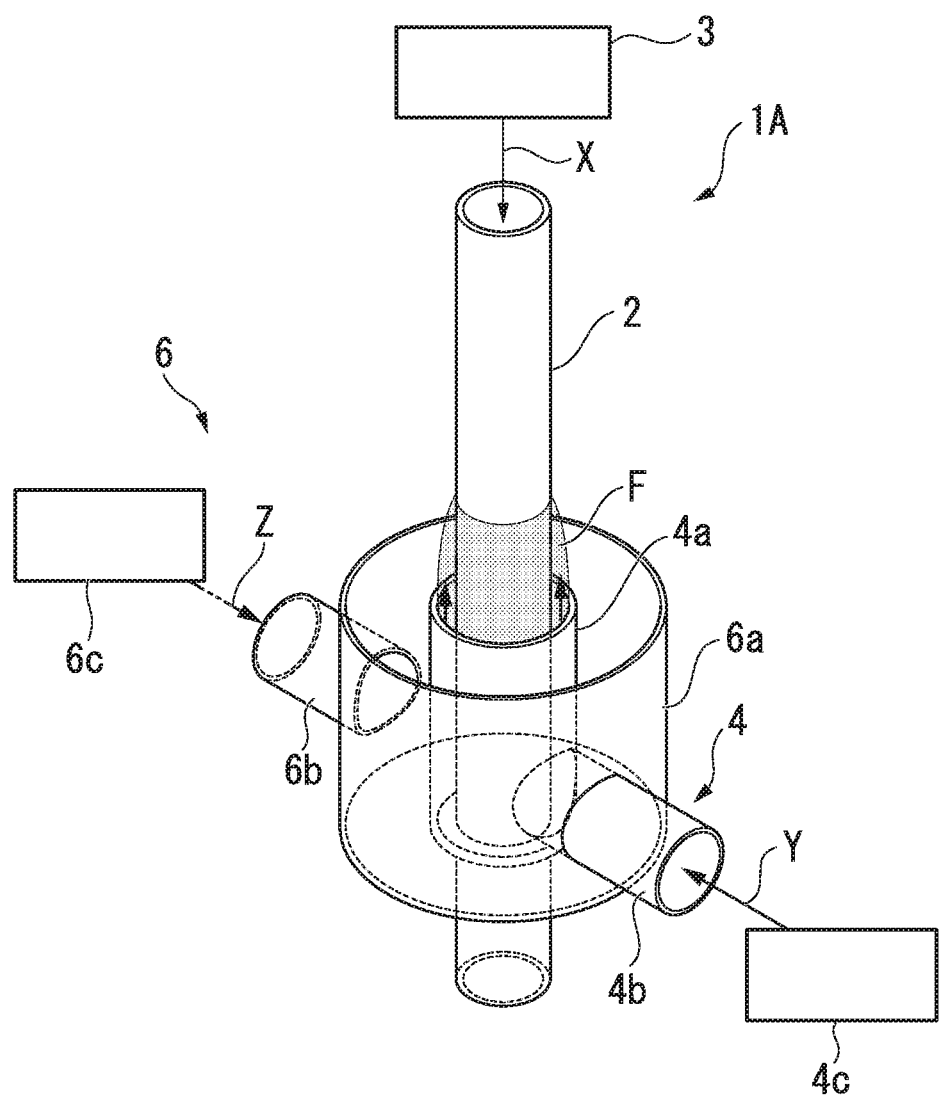
FIG. 3A is a perspective view schematically showing an overall constitution of a combustion experiment device in a second embodiment of the present disclosure.
Figure 3B:
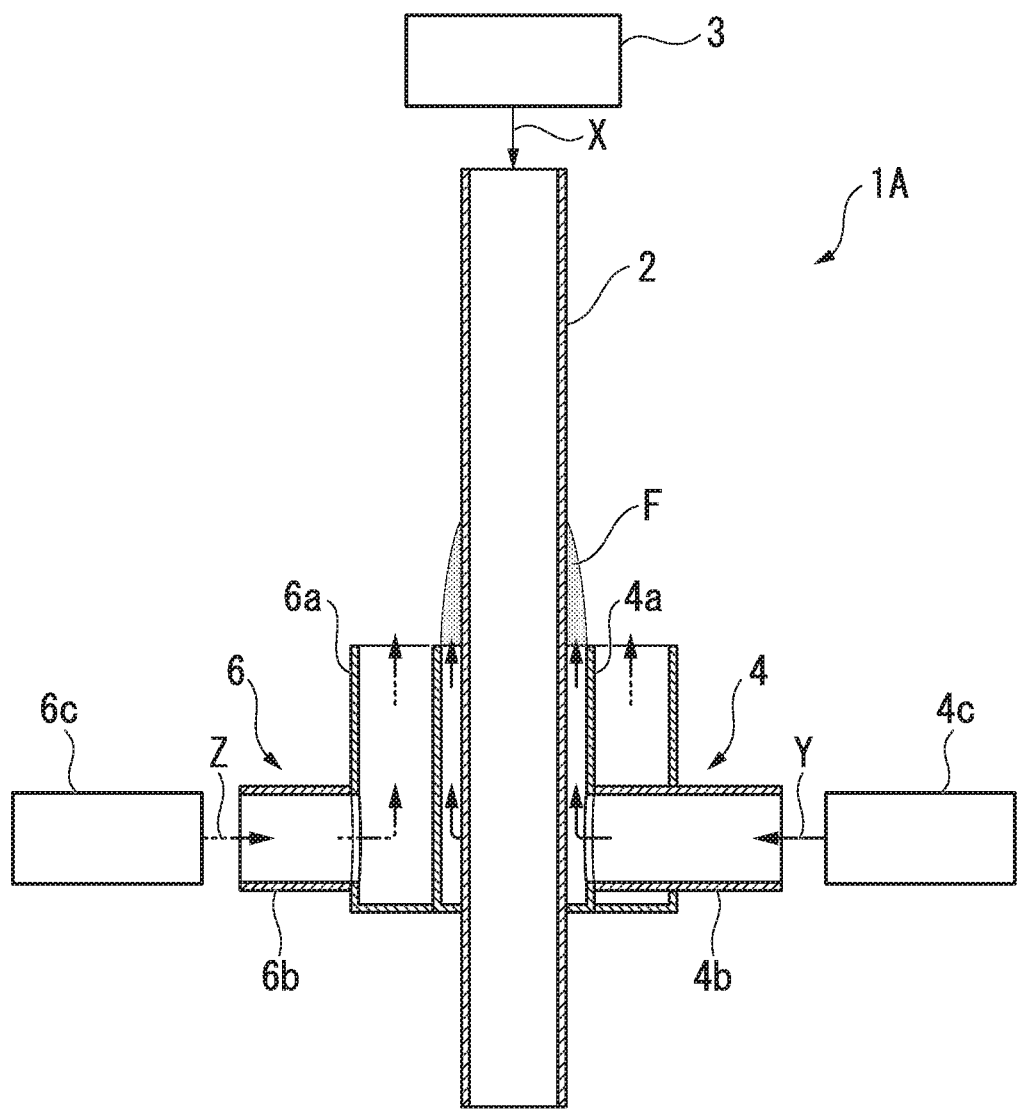
FIG. 3B is a longitudinal sectional view schematically showing the overall constitution of the combustion experiment device in the second embodiment of the present disclosure.

FIGS. 3A and 3B are schematic views showing the whole of a combustion experiment device 1A of the present embodiment wherein FIG. 3A is a perspective view, and FIG. 3B is a longitudinal sectional view. As shown in these figures, the combustion experiment device 1A of the present embodiment is provided with an auxiliary gas feeder 6.

This auxiliary gas feeder 6 is provided with a nozzle part 6a, a feed tube 6b, and an air feeder 6c. The nozzle part 6a is a cylindrical part that covers a nozzle part 4a of a burner part 4 from the outside of a reaction tube 2 in a radial direction. The nozzle part 6a has an upper end acting as an opened end and a lower end acting as a closed end. The nozzle part 6a having this constitution ejects an auxiliary gas Z toward an upstream side (an upper side) of the reaction tube 2. That is, the auxiliary gas feeder 6 flows the auxiliary gas along the reaction tube 2 at the outside of the reaction tube 2 in the radial direction relative to a region to which a combustible gas Y flows.

The nozzle part 6a is a circular tube disposed to be coaxial with respect to an axis L of the reaction tube 2. Thus, an annular flow passage having a uniform size in a circumferential direction is formed between the nozzle part 6a of the auxiliary gas feeder 6 and the nozzle part 4a of the burner part 4. For this reason, the auxiliary gas Z passing through this annular flow passage to be injected from the upper end of the nozzle part 6a is uniformly injected around the reaction tube 2 when viewed in a direction running along the axis L of the reaction tube 2.

The feed tube 6b is a tube that is connected to the nozzle part 6a from the outside of the nozzle part 6a in a radial direction and is intended to feed the auxiliary gas Z to the inside of the nozzle part 6a. A cross-sectional area of the feed tube 6b is set to be greater than that of the annular flow passage formed between the nozzle part 6a of the auxiliary gas feeder 6 and the nozzle part 4a of the burner part 4. Thus, an inlet area of the nozzle part 6a for the auxiliary gas Z is greater than an outlet area, and the auxiliary gas Z is easily uniformly distributed in the nozzle part 6a. Therefore, the auxiliary gas Z can be more uniformly injected around the reaction tube 2.

The air feeder 6c feeds air acting as the auxiliary gas Z to the feed tube 6b. As this auxiliary gas Z, a gas that contains a combustion assisting gas, such as oxygen, and an incombustible gas may be used. In the present embodiment, air is used as a typical example.

This auxiliary gas feeder 6 feeds the air acting as the auxiliary gas Z from the air feeder 6c to the nozzle part 6a through the feed tube 6b, and flows the auxiliary gas Z from the nozzle part 6a around the reaction tube 2. Thus, a flow of the auxiliary gas Z directed toward the upstream side of the reaction tube 2 is formed around a flame F, and the flame F elongates toward the upstream side of the reaction tube 2. As a concentration of the incombustible gas such as nitrogen in the auxiliary gas Z is changed, a spreading and a length of the flame F can be adjusted.

As a ratio between the combustion assisting gas and the incombustible gas which are contained in the auxiliary gas Z varies, a concentration of oxygen given to the flame F varies, and a shape and a temperature of the flame F can be changed. For this reason, the air feeder 6c may be given a function of a component adjusting part that adjusts the ratio between the combustion assisting gas and the incombustible gas. Thus, the shape of the flame F can be arbitrarily modified.

Figure 4A:
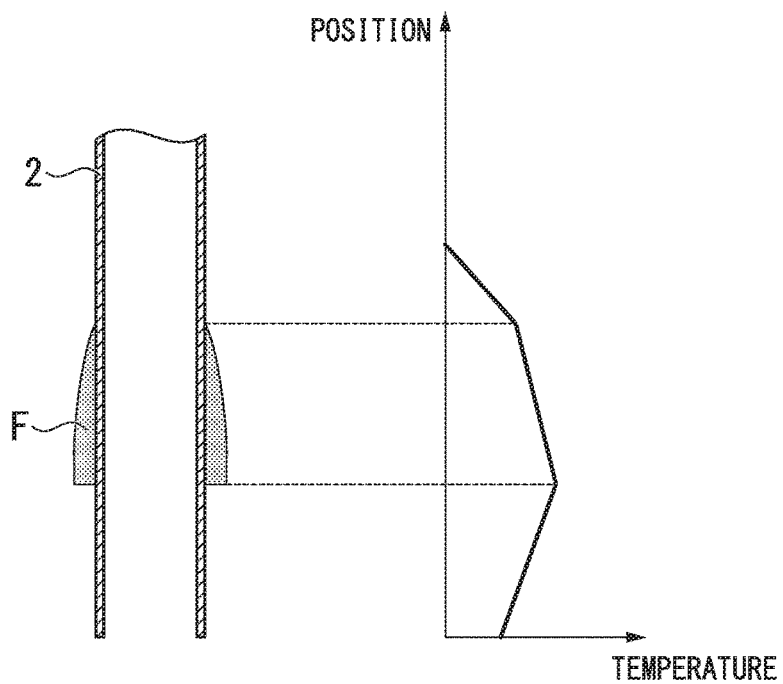
FIG. 4A is a schematic view showing a temperature gradient imparted to the reaction tube in the combustion experiment device in the first embodiment of the present disclosure.
Figure 4B:
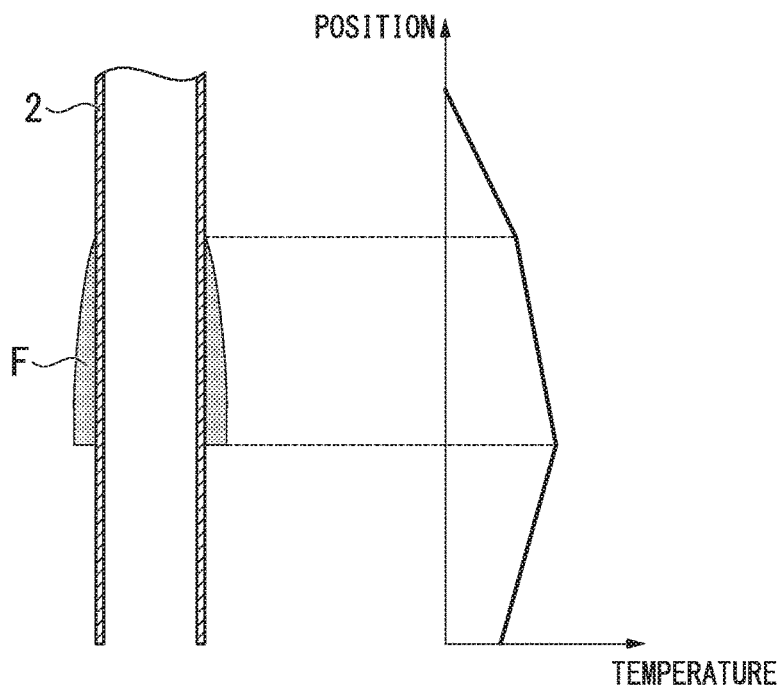
FIG. 4B is a schematic view showing a temperature gradient imparted to a reaction tube in the combustion experiment device in the second embodiment of the present disclosure.

FIG. 4A is a schematic view showing a temperature gradient imparted to the reaction tube 2 in the combustion experiment device 1 of the first embodiment. Also, FIG. 4B is a schematic view showing a temperature gradient imparted to the reaction tube 2 in the combustion experiment device 1A of the present embodiment. As shown in these figures, in comparison with the combustion experiment device 1 of the first embodiment, as the flame F elongates like in the combustion experiment device 1A of the second embodiment, the temperature gradient imparted to the reaction tube 2 is smoothed, and an amount of variation in temperature is reduced with respect to an amount of variation in position of the reaction tube 2. For this reason, information about a temperature corresponding to a position of the flame formed inside the reaction tube 2 can be obtained with higher accuracy, and measurement accuracy can be improved.

While the preferred embodiments of the present disclosure have been described with reference to the drawings, the present disclosure is not limited to the above embodiments. All of the shapes and combinations of the components shown in the aforementioned embodiments are only examples, and can be variously modified based on design requirements, and so on, without departing from the scope of the present disclosure.

Figure 5A:
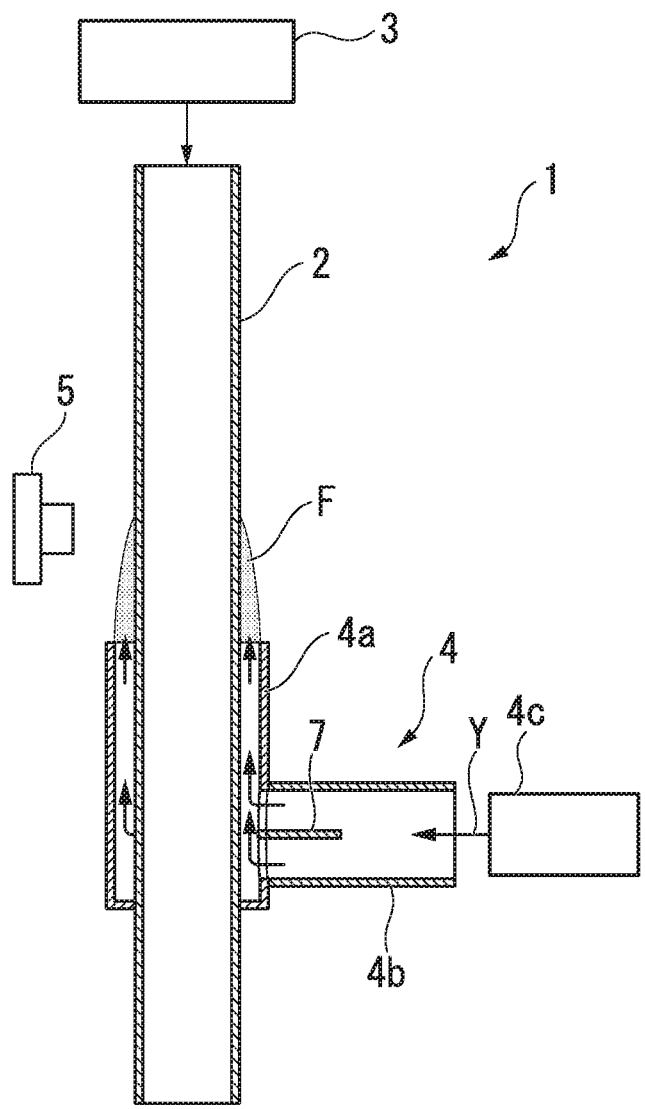
FIG. 5A is a longitudinal sectional view of a first modification of the combustion experiment device in the first embodiment of the present disclosure.

For example, as shown in FIG. 5A, a partition 7 dividing the inside of the feed tube 4b in the radial direction of the feed tube 4b may be installed in the feed tube 4b of the burner part 4. Thereby, since the combustible gas Y is dispersed and fed to the nozzle part 4a of the burner part 4, the combustible gas Y can be more uniformly ejected from the nozzle part 4a.

Figure 5B:
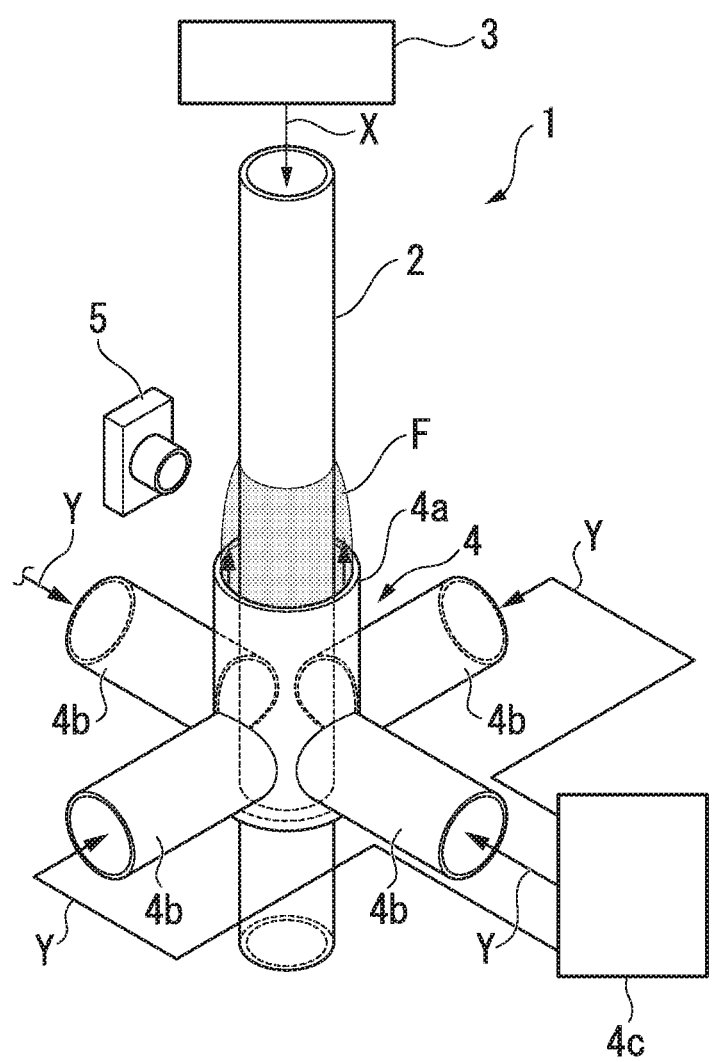
FIG. 5B is a perspective view of a second modification of the combustion experiment device in the first embodiment of the present disclosure.

As shown in FIG. 5B, a constitution in which a plurality of feed tubes 4b are connected to the nozzle part 4a from respective sides in the circumferential direction of the reaction tube 2 may be adopted. Even in this case, since the combustible gas Y is dispersed and fed to the nozzle part 4a of the burner part 4, the combustible gas Y can be more uniformly ejected from the nozzle part 4a.

Figure 5C:
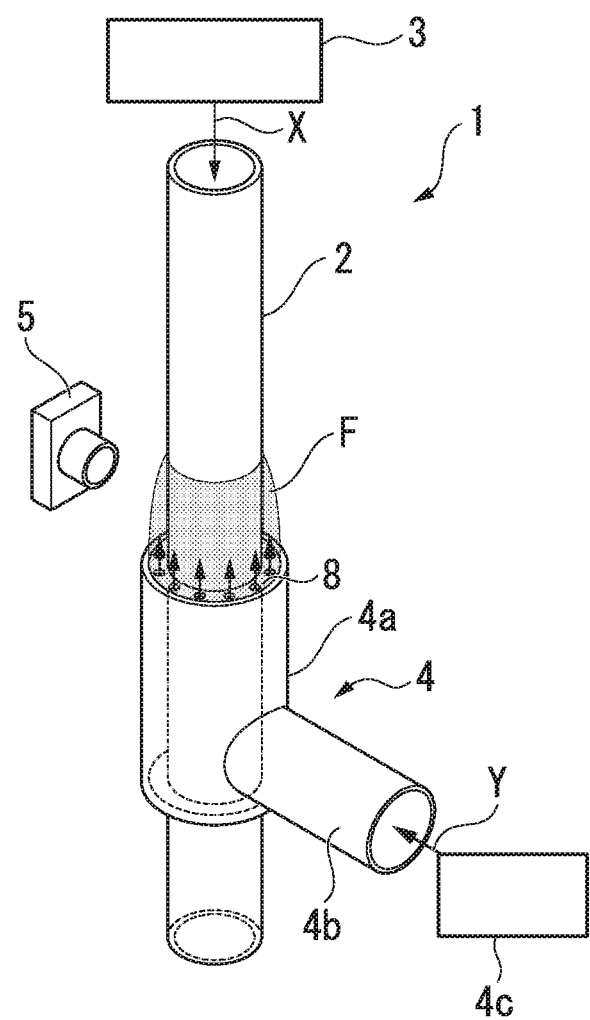
FIG. 5C is a perspective view of a third modification of the combustion experiment device in the first embodiment of the present disclosure.

As shown in FIG. 5C, a dispersion plate 8 having a plurality of through-holes may be installed at the upper end used as the opened end of the nozzle part 4a. Even in this case, the combustible gas Y can be more uniformly ejected from the nozzle part 4a.

The constitutions shown in FIGS. 5A to 5C may be equally applied to the auxiliary gas feeder 6 of the second embodiment. That is, a constitution in which the partition 7 is installed in the feed tube 6b, a constitution in which a plurality of feed tubes 6b are connected to the nozzle part 6a, and a constitution in which the dispersion plate 8 is installed on the nozzle part 6a may be adopted by the auxiliary gas feeder 6 of the second embodiment.

In the above embodiments, the constitution in which a flammable gas free of a combustion assisting gas is used as the combustible gas Y is adopted. However, the present disclosure is not limited to this. A flammable gas (i.e. a premixed gas) containing a combustion assisting gas may be used as the combustible gas Y. In this case, to prevent a flashback, countermeasures which provide a cooling mechanism at the upper end of the nozzle part 4a or sufficiently increase a flow rate of the combustible gas Y ejected from the nozzle part 4a are preferably taken. The flammable gas is not limited to the hydrogen gas.

In the above embodiments, the constitution in which the combustible gas Y is fed to the nozzle part 4a in the radial direction has been described. However, the present disclosure is not limited to this. The feed tube 4b may be connected to the nozzle part 4a in the axial direction of the reaction tube 2, and the combustible gas Y may be fed to the nozzle part 4a in the axial direction. In this case, there is a risk that the hydrogen gas feeder 4c is exposed to an exhaust gas exhausted from the lower end of the reaction tube 2. For this reason, it is possible to bend the lower end of the reaction tube 2 and set a discharge direction of the exhaust gas to a direction different from that of the hydrogen gas feeder 4c.

In the above embodiments, the constitution in which the reaction tube 2 is disposed such that the axial direction thereof becomes the vertical direction and the sample evaluation gas X is fed from the upper end side of the reaction tube 2 has been described. However, the present disclosure is not limited to this. A constitution in which the sample evaluation gas X is fed from the lower end side of the reaction tube 2 may be adopted. In this case, the burner part 4 is disposed to eject the flammable gas downward.

INDUSTRIAL APPLICABILITY

In a combustion experiment device that imparts a temperature gradient to a reaction tube to measure combustion characteristics of a sample fluid, measurement accuracy can be improved.

What is claimed is:

1. A combustion experiment device comprising:
a reaction tube into which a sample fluid flows and to which a temperature gradient in which a temperature rises toward a downstream side is imparted; and
a burner part configured to flow a combustible gas along and around the reaction tube from the downstream side to an upstream side of the reaction tube and to maintain a flame surrounding the reaction tube from an outside of the reaction tube in a radial direction, wherein
the burner part includes
a nozzle part which covers the reaction tube from the outside of the reaction tube in the radial direction and configured to eject the combustible gas, and
a feed tube connected to the nozzle part and configured to feed the combustible gas to the nozzle part.

2. The combustion experiment device according to claim 1, wherein the burner part is configured to flow a flammable gas free of a combustion assisting gas as the combustible gas.

3. The combustion experiment device according to claim 1, wherein a plurality of feed tubes are connected to the nozzle part in a circumferential direction of the reaction tube.

4. The combustion experiment device according to claim 2, wherein a plurality of feed tubes are connected to the nozzle part in a circumferential direction of the reaction tube.

5. The combustion experiment device according to claim 1, comprising a partition which divides an inside of the feed tube in a radial direction of the feed tube.

6. The combustion experiment device according to claim 2, comprising a partition which divides an inside of the feed tube in a radial direction of the feed tube.

7. The combustion experiment device according to claim 3, comprising a partition which divides an inside of the feed tube in a radial direction of the feed tube.

8. The combustion experiment device according to claim 4, comprising a partition which divides an inside of the feed tube in a radial direction of the feed tube.

9. The combustion experiment device according to claim 1, comprising an auxiliary gas feeder configured to flow an auxiliary gas containing a combustion assisting gas along the nozzle part at an outer side of the reaction tube in the radial direction relative to a region to which the combustible gas flows.

10. The combustion experiment device according to claim 9, wherein an incombustible gas is contained in the auxiliary gas.

11. The combustion experiment device according to claim 10, comprising a component adjuster configured to adjust a ratio between the combustion assisting gas and the incombustible gas which are contained in the auxiliary gas.

* * * * *